United States Patent [19]

Bonnot et al.

[11] Patent Number: 4,521,353

[45] Date of Patent: Jun. 4, 1985

[54] PROCESS FOR PRODUCING ENCAPSULABLE GLOBULES

[75] Inventors: Guy Bonnot, Collognes au Mont d'Or; Pierre Laviolette, Chassieu; Andre Potiron, Maurepas; Jean-Yves Deysson, Paris, all of France

[73] Assignee: Institut National de la Recherche Agronomique, Paris, France

[21] Appl. No.: 492,700

[22] Filed: May 9, 1983

[30] Foreign Application Priority Data

May 12, 1982 [FR] France ................................ 82 08288

[51] Int. Cl.³ ................................................ B29C 6/00

[52] U.S. Cl. ........................................... 264/8; 264/12; 264/28; 264/81; 264/298; 425/7; 425/10

[58] Field of Search ................... 264/4, 12, 8, 28, 298, 264/81; 425/5, 8, 10, 7

[56] References Cited

U.S. PATENT DOCUMENTS

| | | | |
|---|---|---|---|
| 1,614,636 | 1/1927 | Wachtel | 425/10 |
| 2,495,147 | 1/1950 | Street | 264/8 |
| 2,766,478 | 10/1956 | Raley, Jr. et al. | 264/4 |
| 2,956,304 | 10/1960 | Batten et al. | 425/10 |
| 3,301,707 | 1/1967 | Loeb et al. | 264/81 |
| 3,379,803 | 4/1968 | Tittmann et al. | 264/81 |
| 3,464,926 | 9/1969 | Vandegarr et al. | 264/4 |
| 3,550,195 | 12/1970 | Campbell | 425/10 |
| 3,646,177 | 2/1972 | Thompson et al. | 264/28 |
| 3,928,515 | 12/1975 | Richmond et al. | 264/8 |
| 4,063,856 | 12/1977 | Dziedzic | 425/8 |
| 4,073,158 | 2/1978 | Guiller | 426/524 |
| 4,286,020 | 8/1981 | Himel et al. | 264/4 |

FOREIGN PATENT DOCUMENTS

| | | |
|---|---|---|
| 2080805 | 11/1971 | France . |
| 2078585 | 11/1971 | France . |
| 2290246 | 11/1974 | France . |
| 2460625 | 7/1979 | France . |
| 1320467 | 6/1973 | United Kingdom . |
| 1340015 | 12/1973 | United Kingdom . |

*Primary Examiner*—Jeffery Thurlow
*Assistant Examiner*—Patrick Dailey
*Attorney, Agent, or Firm*—Karl W. Flocks; Sheridan Neimark

[57] ABSTRACT

Process for producing encapsulable globules by means of a film polymerized in situ, applicable particularly to the production of breeding substrates for entomophagous insects in the form of artificial lepidoptera eggs, in which process drops are frozen for their encapsulation and comprising the stages of: forming a jet of the substance to the frozen and spraying said jet in the form of drops by disintergration of said jet; collecting said drops on a cellular grid which is held at the surface of a bath of cryogenic liquid having a density less than that of said substance; sifting the frozen globules derived from the drops on at least one sieve immersed in the bath beneath said cellular grid.

8 Claims, 2 Drawing Figures

8
3
3
7
6
6
6
4
2
1
5

PROCESS FOR PRODUCING ENCAPSULABLE GLOBULES

BACKGROUND OF THE INVENTION

The present invention relates to a process for the production of encapsulable globules, applicable particularly to the production of breeding substrates for various types of entomophagous insects, in particular artificial lepidoptera eggs useful for the mass breeding of trichogramma. The process is in addition applicable to any fractionation of an artificial medium into small sized units easy to preserve and manipulate without deterioration.

In the case of artificial eggs of lepidoptera, each unit of encapsulated nutrient medium is intended to permit, within the capsule, the development of one or of several organisms which will have been introduced therein, or to serve as a nutritional unit or prey for organisms capable of exploiting them.

For such use, the production of encapsulation is very complex: on the one hand, the medium must satisfy all of the vital processes of the parasite and ensure its survival, its nutrition, its growth, its organogenesis by providing, in a limited space, all the constituents of a viable and fertile adult. On the other hand, the envelope of the capsule must satisfy numerous simultaneous requirements such as size of eggs, thickness and consistency of the shell, permeability to gases, impermeability to water, inertia with respect to the constituents of the medium; it must in addition permit a normal oviposition.

Taking into account however, the composition of the media to be coated, which are constituted by several tens of suitable compounds of which a part is in the form of a particularly fragile lipid emulsion, the encapsulation cannot be effected by means of the coacervation known in other fields, but by the deposition in vapor phase of a substance polymerizable into a thin film on frozen globules. Due to the fact however of the composition recalled above of the medium to be frozen, it was necessary to develop a production process for such globules.

SUMMARY OF THE INVENTION

It is accordingly an object of the present invention to provide such a process, applicable to substances of very varied nature to be frozen and which may be constituted by organic and/or inorganic solutions, which may or may not contain suspended colloidal particles, as well as emulsions of immiscible phases.

According to the invention, the substance to be frozen is sprayed by disintegration of a jet onto a cellular grid held at the surface of a bath of cryogenic liquid having a density less than that of said substance, and the frozen globules are sifted onto at least one sieve immersed in the bath beneath said cellular grid.

BRIEF DESCRIPTION OF THE DRAWINGS

Other features and advantages of the invention will emerge better from the description which follows, with reference to the accompanying drawings in which.

In these drawings, the same reference numerals denote the same elements.

DESCRIPTION OF THE PREFERRED EMBODIMENTS

Figure 1:
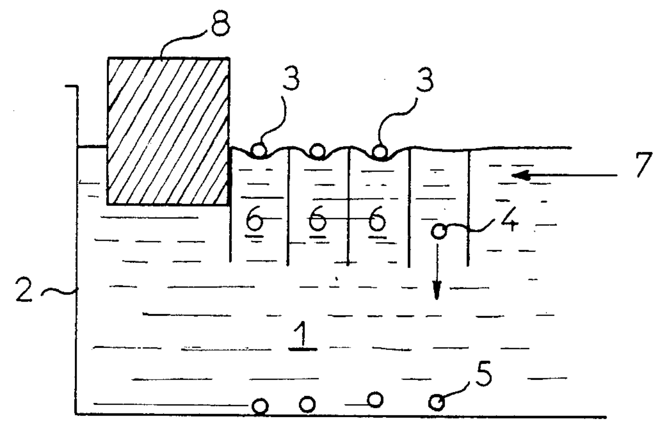
FIGS. 1 and 2 show diagrammatic views of apparatus illustrating the freezing process according to the invention.

Referring to FIG. 1, the advantageous cryogenic liquid is liquid nitrogen constituting a bath 1 contained in a vessel 2. As indicated above, the medium to be frozen has a relatively long freezing time, prohibiting, for example, the freezing technique of drops in free fall into a cold gas, which would lead to a prohibitive dropping height. According to the invention, a drop 3, in spite of its greater density than that of bath 1, floats to the surface of the bath by a calefaction phenomenon. The "calefaction phenomenon" is due to the intense vaporization of the cryogenic liquid resulting from the high difference of temperature between the droplet which is substantially at the ambient temperature and said cryogenic liquid. According to this known phenomenon the droplet is gas-borne in quick erratic rotation, allowing a perfect spherical shape to be formed, until deep freezing into a globule 4. When the thermic equilibrium is quite established. When on the contrary, the drop is frozen into a globule 4, calefaction ceases and it falls to the bottom of the vessel 2 (at 5) from which it is extracted by any suitable means known in itself. It is possible of course to replace the nitrogen by any other suitable liquified gas.

When several neighbouring drops float to the surface of the same bath, they have a tendency to group together. To avoid this agglomeration, each drop 3 is isolated from its neighbours in a cell 6 of a grid 7 of the bee's nest or honeycomb type, which is held at the surface of the bath 1, by means of a float 8.

Figure 2:
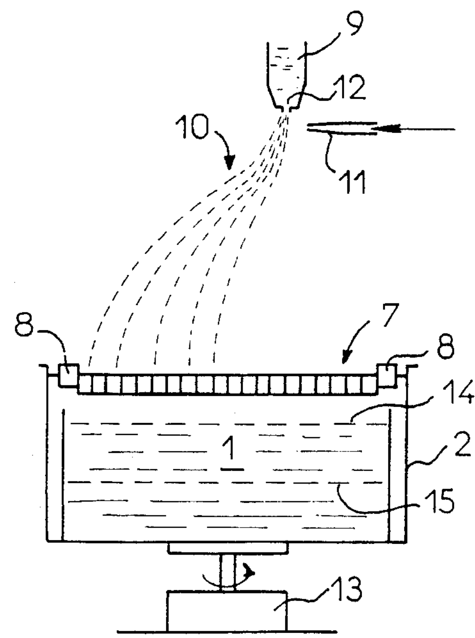

Referring to FIG. 2, the substance to be frozen flows from a reserve 9 and it is sprayed into a jet 10 by means of a pneumatic nozzle 11. Of course, the jet 10 has emerged from a calibrated orifice 12 whose diameter is a function of the desired globule dimension. For example, in the case of artifical eggs of lepidoptera, the diameter of the globules may be comprised between 0.3 and 1.5 mm according to the species.

In addition a rotation is imparted to bath 1 by means of a motor 13. The rotation of the bath, associated with the pneumatic dispersion of the jet 10 enables the circumstance to be avoided of two drops 3 falling into the same cell 6 during freezing. As indicated above, the frozen globules 4 are sifted during their fall into the bath 1 onto at least one suitably calibrated sieve 14, 15, immersed in the bath beneath the cellular grid 7.

The encapsulation of the frozen globules obtained by means of the process as described above is carried out in manner known in itself by in situ polymerisation, under vacuum and low temperature, of a monomer obtained, for example, from di-paraxylylene or 2,2-paracyclophane, after sublimation and pyrolysis of this compound by passage into suitable successive ovens. The globules are introduced into the deposition vessel through a lock, itself held at low temperature, and they are deposited preferably in a vibrating container in order to avoid the sticking of the frozen particles to the walls.

An encapsulation compound can be employed resulting, for example, from the production process which will be described below and consisting essentially, from dichloro$\alpha,\alpha'$-paraxylene, of forming the dimercaptomethyl 1,4 benzene, condensing the latter with the dichloro$\alpha,\alpha'$-paraxylene, then carrying out a photochemical desulfuration of the condensation product in the presence of triethylphosphite.

The following examples, given by way of explanation but which are to be taken as in no way limiting, give the reaction details useful for the preparation of the encapsulation 2,2-paracyclophane, as well as illustration of the process according to the invention for the production of globules of various composition and purpose.

EXAMPLE 1

Review of the synthesis of 2,2-paracyclophane:

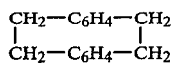

(tricyclo 8,2,2,2$^{4,7}$ hexadeca 4,6,10, 12, 13, 15 hexaene).

The raw material is dichloro$\alpha,\alpha'$paraxylene which is a commercial product.

The various steps of the synthesis are as follows:

(1) Synthesis of dimercapto-methyl -1,4 benzene:

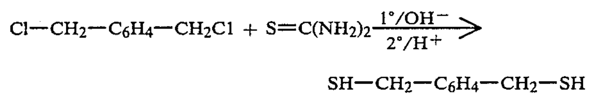

(2) Condensation of dimercapto-methyl -1,4 benzene with $\alpha,\alpha'$ dichloro paraxylene in a dilute medium and in the presence of soda

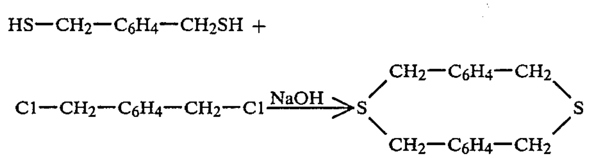

(3) Photochemical desulfuration in the presence of triethylphosphite

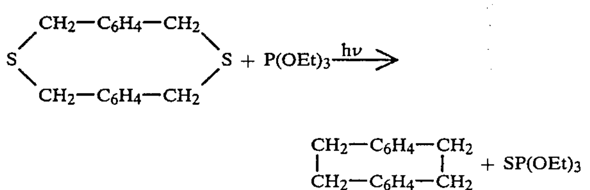

Operational Method

Step 1

To a solution of $\alpha,\alpha'$ dichloro paraxylene (87.5 g–0.5 mol) in isopropanol (350 ml) are added with stirring a solution of thiourea (95 g–1.25 mol) in water (150 ml). It is then brought to reflux, still with stirring, for 30 minutes. After cooling, 125 ml of 21% ammonia are poured in, it is again heated for 30 minutes under reflux and acidified with concentrated hydrochloric acid.

The crystalline mass obtained is filtered, washed with cold water and recrystallised in 300 ml of hexane.

Weight obtained: 76 g. Yield: 90%.

Step 2

Into a 6 liter reactor, there are brought to reflux 4.4 liters of 95% alcohol. Simultaneously there are poured in at identical rates, two solutions:

10.5 g (60 mmoles) of $\alpha\alpha'$ dichloro paraxylene in 500 ml of benzene.

10.2 g (60 mmoles) of para dimercapto-methyl benzene and 4.8 g of NaOH in 500 ml of 95% alcohol (it is necessary to obtain this solution to disolve the soda NaOH in the minimum of water (5 ml)).

Speed of addition must be slight in order to avoid the intermolecular condensation reaction.

A speed of 50 ml/h is preferred. Operation is at a flow-rate of 100 ml/h per portion of 100 ml, with interruptions between the additions, the 500 ml being poured in in 8 hours.

After the end of the addition, the reflux is maintained one night (14 hours), then the solvents are evaporated (4 to 5 hours). The residue is extracted, hot, twice with 250 ml of benzene.

On cooling of these benzene solutions there is crystallisation of the product which is collected by filtration (8 to 9 grams).

The filtrate is then evaporated, the residue is recrystallised in chloroform (2 g in 30 cm$^3$). About 1 g of product is recovered.

Weight obtained 10 g; yield 62%

Melting point: 284° C.

NMR ($CDCl_3$)$\delta$=3.75 ppm (8H) $\delta$=6.85 ppm (8H).

Step 3

For supplying the light energy, a high pressure mercury vapor lamp of 400 watts is used.

5 g of sulfurised heterocycle compound are suspended in 500 cm$^3$ of triethylphosphite by magnetic stirring and a current of nitrogen. The period of irradiation is 2 hours, during which a cooling flow of water is necessary. Too long a period of irradiation reduces the yield. There is complete dissolution.

The solvent is evaporated under slight vacuum (20 mm) and the evaporation is terminated under more intense vacuum.

Triethylphosphite: BP=150° C. at atmospheric pressure.

SP $(OEt)_3$: B.P.$_{20}$=106° C.

The residue is taken up again with a little acetone (10 ml) and it is filtered. The residue recovered (3 g) is recrystallised in toluene (70 ml). 2.2 g of white product is obtained with correct melting point (285° C.), with a NMR spectrum also in accordance with the literature. However this product contains an impurity which is fluorescent in UV, which is not removed by sublimation. Its elimination is done by filtration over silica.

A solution of 2 g in 300 ml of benzene is passed over a column of 2 cm diameter filled with 15 g of silica. The impurity does not migrate. To recover the whole of the paracyclophane it is necessary to elute with 300 ml of benzene.

To increase the yields: recrystallisation in toluene is done after grouping together from several irradiations.

From the residues of recrystallisation in toluene and from the washing filtrates with acetone, paracyclophane can be recovered (3 operations—0.6 g).

Paracyclophane: M.P.=285° C. (sublimation)

NMR ($CDCl_3$) $\delta$=3.15 (8H) $\delta$=6.60 (8H).

EXAMPLE II

By means of the process according to the invention microglobules of artificial medium having a composition close to that of the content of the egg of the lepidoptera *Ephestia kuehniella* are prepared, namely particularly 10% of proteids principally in proteinic form and 10% lipids in emusion stabilised by egg lecithin. The substance to be frozen in this case is organic and consists of an emulsion of two immiscible phases.

These microglobules, intended after encapsulation in a suitable polymerised film, to serve as a host or artificial eggs for laying and development of oophage parasites such as Trichogramma, have a diameter comprised between 0.6 and 1 mm, so as to limit a volume close to that of the eggs of lepidoptera which serve for the usual hosts.

EXAMPLE III

In the same way as in Example II, microglobules are prepared in which the substance to be frozen or the encapsulated medium, known in itself, in composed of of chicken egg yolk (2 volumes), insect hemolymph (3 volumes) and saline solution (1 volume). In this case, the substance to be frozen comprises an organic fraction and an inorganic fraction, with suspended colloidal substances.

EXAMPLE IV

Again in the same manner, microglobules are prepared of which the substance to be frozen is either a complete ground product of aphids, or a complex artificial medium intended to replace the latter, and it can include at the same time an organic fraction, an inorganic fraction and colloids. After encapsulation, the microglobules obtained have a diameter comprising between 1 and 2 mm and they constitute artificial prey or artificial aphids, intended for the breeding of aphidiphage predators such as coccinella, chrysopes etc.

It is of course well understood that the present invention has only been described and illustrated by way of explanation but which is in no way limiting and that any useful modification could be introduced therein, particularly within the field of technical equivalents, without departing from its scope.

What is claimed is:

1. Process for producing generally spherical globules, subsequently encapsulable by means of a film polymerised in situ, applicable particularly to the production of breeding substrates for entomophagous insects in the form of artificial lepidoptera eggs, in which process drops are frozen for their encapsulation, and comprising the stages of:

forming a jet of a substance to be frozen in the form of drops and spraying said jet by dispersion of said jet;

collecting said drops on a grid, provided with cells which is held at the surface of a bath of cryogenic liquid having a density less than that of said substance;

floating said drops on the surface of said bath by a calefaction phenomenon, each drop isolated in a cell of said grid until freezing, so as to form generally spherical frozen globules;

sifting the frozen globules derived from the drops on at least one sieve immersed in the bath beneath said cellular grid.

2. Process according to claim 1, wherein the cryogenic liquid bath is constituted by a liquefied gas such as nitrogen.

3. Process according to claim 1, wherein the jet is derived from a reserve provided with a calibrated orifice, the diameter of said calibrated orifice being a function of the dimensions of the globules to be obtained.

4. Process according to claim 1, wherein the jet is sprayed by means of a pneumatic nozzle and the cryogenic bath is rotated, in order to avoid agglomeration of the drops to be frozen.

5. Process according to claim 1, wherein the substance to be frozen is constituted by an organic solution which can contain suspended colloidal substances.

6. Process according to claim 1, wherein the substance to be frozen is constituted by an inorganic solution which can contain suspended colloidal substances.

7. Process according to claim 1, wherein the substance to be frozen is constituted by an emulsion of two immiscible phases.

8. Process according to claim 1, wherein the film polymerised in situ is constituted by 2,2-paracyclophane.

* * * * *